United States Patent [19]

Steeg et al.

[11] Patent Number: 5,770,386

[45] Date of Patent: Jun. 23, 1998

[54] METHODS AND COMPOSITIONS FOR INCREASING THE SENSITIVITY OF A CELL TO A DNA DAMAGING AGENT

[75] Inventors: Patricia S. Steeg, Ellicott City; Lance A. Liotta, Potomac; Ursula Flatow, Bethesda, all of Md.

[73] Assignee: The United States of America as represented by the Department of Health and Human Services, Washington, D.C.

[21] Appl. No.: 886,368

[22] Filed: May 20, 1992

[51] Int. Cl.$^6$ ..................... G01N 33/574; G01N 33/573; C12Q 1/00

[52] U.S. Cl. ................ 435/7.23; 435/6; 435/15; 435/29; 435/32; 435/172.1; 435/172.3; 435/7.4; 436/63; 436/64; 436/813

[58] Field of Search .................. 435/6, 15, 7.23, 435/172.1, 172.3, 32, 29, 7.4; 436/63, 64, 813; 530/387.7

[56] References Cited

U.S. PATENT DOCUMENTS 5,049,662  9/1991  Steeg et al. ........................ 536/27

OTHER PUBLICATIONS

Biggs et al., "A Drosophila Gene that is Homologous to a Mammalian Gene Associated with Tumor Metastasis Codes for Nucleoside Diphosphate Kinase," *Cell* 63:933–940 (1990).

Chu and Chang, "Xeroderma Pigmentosum Group E Cells Lack a Nuclear Factor that Binds to Damaged DNA," *Science* 242:564–567 (1988).

Chu and Chang, "Cisplatin–Resistant Cells Express Increased Levels of a Factor that Recognizes Damaged DNA," *Proc. Natl. Acad. Sci. USA* 87:3324–3327 (1990).

Leone et al., "Reduced Tumor Incidence, Metastatic Potential, and Cytokine Responsiveness of nm23–Transfected Melanoma Cells," *Cell* 65:25–35 (1991).

Patterson and Chu, "Evidence that Xeroderma Pigmentosum Cells from Complementation Group E are Deficient in a Homolog of Yeast Photolyase," *Molecular and Cellular Biology* 9:5105–5112 (1989).

Rosengard et al., "Reduced Nm23/Awd Protein in Tumour Metastasis and Aberrant Drosophila Development," *Nature* 342:177–180 (1989).

Stahl et al., "Identification of a Second Huan nm23 Gene, nm23–H2," *Cancer Research* 51:445–449 (1991).

Steeg et al., "Evidence for a Novel Gene Associated with Low Tumor Metastatic Potential," *Journal of the National Cancer Institute* 80:200–204 (1988).

Wallet et al., "Dictyostelium Nucleoside Diphosphate Kinase Highly Homologous to Nm23 and Awd Proteins Involved in Mammalian Tumor Metastasis and Drosophila Develoment," *Journal of the National Cancer Institute* 82:1199–1202 (1990).

Ghiorghis, A., et al., *Proc. Annu Meet Am Assoc Cancer Res*, vol. 32, Abstract No. A2567, 1991.

*Primary Examiner*—Toni R. Scheiner
*Attorney, Agent, or Firm*—Needle & Rosenberg, PC

[57] ABSTRACT

The invention provides a method of increasing the sensitivity of a cell to a DNA damaging agent comprising increasing the amount of an NM23 in the cell. The method is especially useful for increasing the sensitivity of tumor cells to chemotherapy and radiation.

17 Claims, 3 Drawing Sheets

METHODS AND COMPOSITIONS FOR INCREASING THE SENSITIVITY OF A CELL TO A DNA DAMAGING AGENT

BACKGROUND OF THE INVENTION

Various references and patents are cited below. The full disclosure of these references is hereby incorporated by reference into the application to more fully describe the state of the art.

NM23 is a protein which was identified based on its reduced expression in highly metastatic tumor cells. U.S. Pat. No. 5,049,662, filed Oct. 13, 1987 and issued Sep. 17, 1991, describes the first successful cloning of nm23 as well as predicting metastatic potential from nm23 RNA levels (see also Leone et al., Cell 65:25–35 (1991)). Nm23 was subsequently shown to be homologous to Dictyostelium nucleoside diphosphate kinase (hereinafter "NDPK") (Wallet et al., J. Natl. Cancer Inst. 82:1199–1202 (1990)). NDPKs were long known to transfer a terminal phosphate from a nucleoside triphosphate to a nucleoside diphosphate. Two closely related forms of human nm23, nm23-H1 and nm23-H2, have been identified which are about 90% homologous at the DNA level (Rosengard et al., Nature 342:177–180 (1989); Stahl et al., Cancer Res. 48:6550–6554 (1991)).

Chu and Chang, Science 242:564–567 (1988) identified a nuclear factor that binds damaged DNA, and is absent in the E complementation group of xeroderma pigmentosum patients. This factor, termed "XPE-BF", is thought to be involved in the recognition step of DNA excision repair. A functional homolog of XPE-BF is the yeast photolyase, a photo-reactivating enzyme that repairs pyrimidine dimers (Patterson and Chu, Mol. Cell-Biol. 9:5105–5112 (1989)).

Tumor cell lines grown in progressively increasing concentrations of cisplatin, a DNA-damaging chemotherapeutic drug, were tested for nuclear XPE-BF levels (Chu and Chang, P.N.A.S. 87:3324–3327 (1990)). The HeLa-R1 cell line was found to be 4.7-fold more resistant to cisplatin inhibition of growth than parental HeLa cells, and concurrently exhibited a 4-fold increase in XPE-BF level. However, the further selection in cisplatin of the HeLa-R3 cell line, which was 14-fold more resistant to cisplatin inhibition of growth than parental cells, was not accompanied by a further increase in XPE-BF level.

The present invention provides the surprising discovery that increased expression of nm23 increases the susceptibility of a cell for chemotherapy and radiation therapy. Further, the subject data shows increased expression of nm23 can result in reduced levels of XPE-BF. Thus, the invention provides an exciting means to increase the susceptibility of tumor cells to DNA damaging agents. Further, because drug resistance is a major reason for failure of radiation and chemotherapy, the invention provides a much needed means to reduce tumor cell resistance to these therapies.

SUMMARY OF THE INVENTION

The invention provides a method of increasing the sensitivity of a cell to a DNA damaging agent comprising increasing the amount of NM23 in the cell. The method is especially useful for increasing the sensitivity of tumor cells to chemotherapy and radiation.

DETAILED DESCRIPTION OF THE INVENTION

Figure 1:
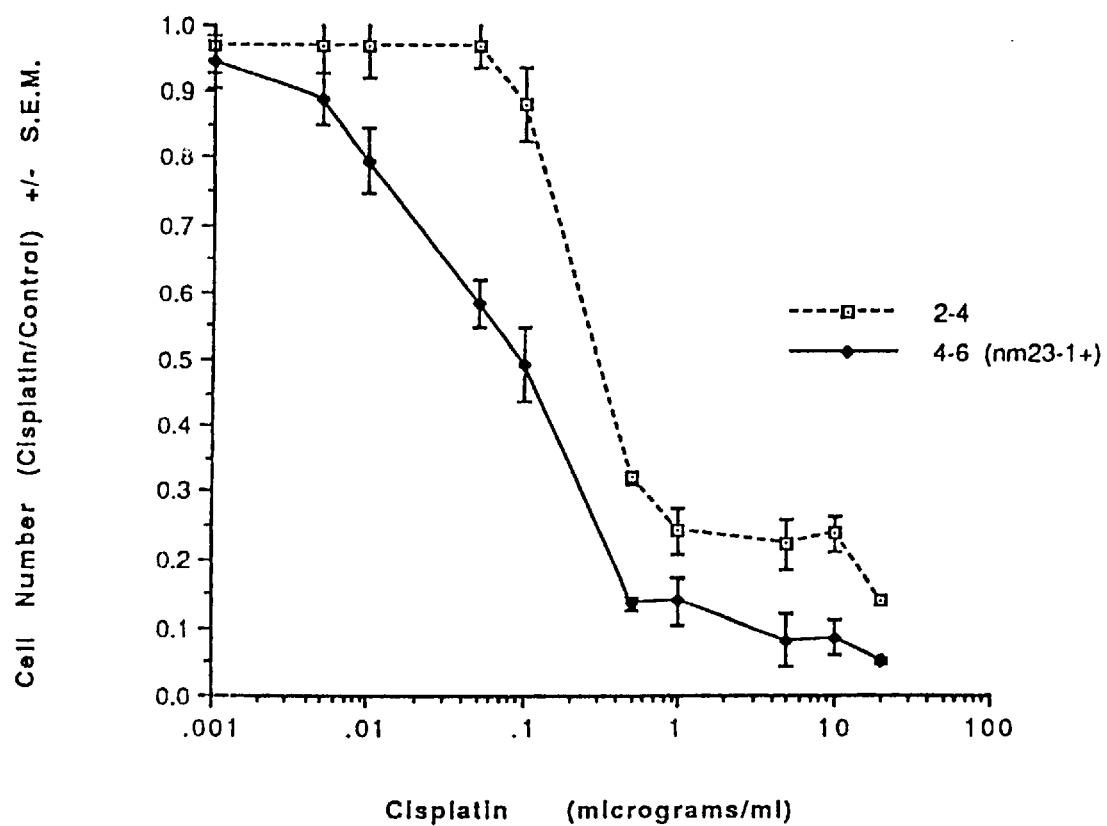
FIG. 1 shows cisplatin sensitivity of the murine K-1735 TK control 2-4 and NM23 expressing 4–6 cell clones in vitro. Cells were incubated in the indicated doses of cisplatin for two days, and viable cell numbers per culture determined using trypan blue exclusion and hemocytometer counting. The data are shown as the mean±S.E.M. ratio of cisplatin treated, divided by cisplatin untreated cells.

This invention provides a method of increasing the sensitivity of a cell to a DNA damaging agent comprising increasing the amount of NM23 in the cell. The core discovery, as shown in the examples, is that by increasing NM23 in a cell, the cell is much more sensitive to DNA damaging agents such as chemotherapeutics and radiation. Thus, by "increasing the sensitivity" is meant that the average dosage of the DNA damaging agent required to inhibit tumor cell growth or to produce a cytotoxic effect is decreased. Also, "increasing the sensitivity" means that the average dosage of the DNA damaging agent administered before the cell exhibits resistance is increased.

As can be appreciated by the core discovery, the precise way in which the amount of NM23 is increased is not critical. Typically, the amount of NM23 is enhanced by something which increases the expression of NM23 in a cell. One method which is exemplified in the examples is transfecting a cell with a vector encoding the nm23 gene which is capable of expressing NM23 protein in the cell. For in vivo uses, this vector could be a virus which infects the cell and causes integration of the nm23 encoding nucleic acid so as to effect transcription. This method is well known in the art. For example, Rosenberg et al., NEJM 323:570–578 (1990), have described viral vectors for the introduction of genes into cells ex vivo. Similar constructs can be utilized in vivo, with minor modifications, to improve their stability and for tissue specific expression. Other methods of increasing transcription include utilizing compounds such as a drug, cytokine or hormone which promotes transcription of the nm23 gene. For example, these compounds can be screened in the presence of the gene encoding nm23. Any compound resulting in increased NM23 expression can be used to treat cells to increase NM23 expression. Screening such compounds is well known in the art. Briefly, a cell line, such as the human MDA-MD-435 breast carcinoma cell line, which expresses low levels of NM23-H1 and NM23-H2, can be used. Cells can be plated in microtitre dishes and incubated with various drugs. After incubation, the culture medium is removed and the cells lysed. NM23 protein levels in the cell lysate can be quantitated using monoclonal or polyclonal antibodies to NM23 in an ELISA or similar assay. As a positive control, the amount of NM23 protein in the transfected H1-177 clone of MDA-MD-435 can indicate the amount of NM23 protein expression associated with marked cisplatin sensitivity.

As also can be appreciated from the core discovery and examples, the sensitivity to virtually any suitable DNA damaging agent can be increased by increasing the amount of NM23 in the cell. Thus, while the examples are directed to the use of cisplatin as the DNA damaging agent, any agent which is made more effective through the increased expression of NM23 is within the scope of the invention. Other suitable DNA damaging agents can be tested in the method utilized for cisplatin in the examples. Moreover, while only cisplatin is exemplified, other DNA damaging agents can routinely be tested, and the scope of claims includes only those DNA damaging agents which are made more effective through increased NM23.

Likewise, the examples set forth below are directed to the use of NM23-H1. However, due to the high homology between NM23-H1 and NM23-H2, NM23-H2 would also be effective in the method. Therefore, by "NM23" is meant any portion of the protein which increases the sensitivity of a cell to a DNA damaging agent. NM23-H2 and any other portion of an NM23 can routinely be tested for activity using the methods set forth in the examples. Fragments of an NM23, like any protein, can be made and the activity tested by routine methods. Briefly, site-directed mutagenesis of the NM23 protein, in which amino acids of the NM23 protein are changed, can be undertaken. The mutagenized constructs can be transfected into tumor cells, and the sensitivity to cisplatin determined. When a specific amino acid is found that abrogates the sensitivity-enhancing activity of NM23, this part of the protein is a candidate active fragment. Confirmation involves cloning fragments of the protein, on a translation start site, into tumor cells, and determination of the cisplatin resistance or sensitivity of the transfected and parental cells. Alternatively, the nm23 gene can be synthesized with insertions or deletions, expressed, and screened for activity.

While the sensitivity of any cell can be increased using the present method, typically the target of increased sensitivity will be tumor cells. This increased sensitivity can be utilized to more effectively eradicate the tumor from a subject. The examples utilize various cells including melanoma and carcinoma cell lines. While the data set forth herein is in vitro, the data is predictive of increasing sensitivity in vivo. Many examples exist in the art concerning DNA repair where in vitro data was predictive of in vivo success. (See, for example, Foster et al., *Pharmacol* 22:147–152 (1988); Poirier et al., *P.N.A.S.* 79:6443–6447 (1982); Hansson et al., *Cancer Research* 51:3384–3390 (1991); Kinsella and Haran, *Cancer Research* 51:1855–1859 (1991); and Hancock et al., *Cancer Research* 51:4575–4580 (1991)).

The invention also provides a method of decreasing the activity of a DNA repair enzyme or factor in a suitable cell comprising increasing the amount of NM23 in the cell. Thus, one possible mechanism through which the increased sensitivity of a cell to a DNA damaging agent can be accomplished is by binding, preventing transcription of, or otherwise inactivating repair enzymes, such as XPE-BF. However, the mechanism through which NM23 acts to increase a cell's sensitivity to a DNA damaging agent is not limited to this mechanism.

Also provided is a method of screening drugs for chemotherapeutic DNA damaging activity comprising contacting the drug with a cell having low NM23 and determining the effect on the cell. This method provides a means to utilize a cell line which is resistant to chemotherapy to test the benefits of a potential chemotherapeutic. Therefore, a more accurate prognosis for success is realized.

Also provided is a method of detecting resistance to a DNA damaging agent comprising detecting the amount of NM23 expression in a cell, correlating the amount to an amount for a resistant cell, the presence of NM23 in an amount about equal to or less than the resistant cell indicating resistance. The amount of NM23 in a typical resistant cell can be ascertained by routine testing of amounts of NM23 in various cell types known to be resistant. The cell of interest is then compared to this amount to determine its susceptibility to chemotherapy or radiation therapy.

This invention further provides a method of predicting tumor response to a DNA damaging therapy comprising determining the amount of NM23 in a tumor cell from the patient, correlating the amount of NM23 in the cell to an amount in cells susceptible to the therapy, the presence of NM23 in an amount about equal to or greater than a susceptible cell indicating responsiveness to the therapy. This method also follows from the core discovery provided herein. The method allows a means to prescreen a patient's tumor cells for the most effective therapy.

The invention also provides a kit for modulating the sensitivity of a cell to a DNA damaging agent comprising a means to enhance transcription of NM23 in an amount to increase the sensitivity of the cell to the agent, and a pharmaceutically acceptable carrier. Thus, the kit would include, for example, a vector such as a virus, containing nm23 with suitable sequences for expression. Other means to enhance transcription include drugs, cytokines, and hormones which can be administered to the cell. The amounts of these compounds and vectors can be arrived at by routine testing and are amounts not previously known in the art. A suitable carrier, for example, is phosphate buffered saline.

Finally, the invention provides a kit for detecting the susceptibility of a cell to a DNA damaging therapy comprising a means to detect the amount of NM23 in the cell and a means to correlate the amount of NM23 to an amount known to be susceptible to DNA damaging therapy. The means to detect the amount of NM23 includes many well known methods such as an antibody specifically reactive with NM23. The means to correlate can be data of known susceptibility amounts as described above.

The following examples are intended to illustrate but not limit the invention.

EXAMPLE 1

Expression of NM23 results in reduced levels of the DNA binding factor XPE-BF.

The K-1735 TK melanoma cell line was cotransfected with murine nm23-1 cDNA linked to a constitutive SV40 early promoter and the pRSVneomycin resistance gene as a marker as described in Leone et al., *Cell* 65:25–35 (1991). As controls, TK cells were transfected only with pRSV neomycin resistance, or were cotransfected with nm23-1 and pRSVneo, and clones selected that did not express the NM23-1 construct (Leone et al., *Cell* 65:25–35 (1991)). Two transfection experiments were performed with murine K-1735 TK cells using two different passages of the TK cell line which differed in tumor metastatic potential. One set of stable, high NM23-1 expression and control clones was derived from passage 35 of the TK cell line, and designated 4-6 and 2-4, respectively. Another set of stable, high NM23-1 expression and control transfected TK clones was produced from passage 10 of the TK cell line, and was designated A3 and A2, respectively. Expression of the transfected nm23-1 cDNA in the 4-6 and A3 clones was verified by the presence of a higher molecular weight nm23 RNA transcript on Northern blots in addition to the endogenous 0.8 kb nm23 RNA. In addition, the 4-6 and A3 nm23-1 transfected clones exhibited greater synthesis of immunoprecipitable NM23 protein than did the 2-4 and A2 control clones, respectively (Leon et al., supra).

$6 \times 10^6$ viable cells from the nm23-1 transfected 4-6 clone, the control 2-4 clone, the nm23-1 transfected A3 clone, and the A2 control clone were frozen in 90% (v/v) culture medium, 10% (v/v) DMSO by traditional methods. Nuclear extracts were prepared from these frozen cells. 0.6 µg of nuclear extract was incubated with 0.2 ng of labelled DNA (the 148 bp PvuII-HindIII fragment from the 5' flanking and coding region of the bacterial chloramphenical acetyl transferase gene (f148 in Patterson and Chu, supra.), which was irradiated with 6,000 J/m² from a germicidal UV lamp and end labelled with $^{32}$P-dATP using Klenow polymerase to fill in the 5' overhang left by HindIII). 40 ng of the alternating copolymer poly (dl-dC)-poly (dl-dC) and 20 ng salmon sperm DNA were added to mask nonspecific DNA binding. Reactions were carried out in a final volume of 10 µl at room temperature for 45 min in buffer containing 12% glycerol, 12 mM HEPES (pH 7.9), 60 mM KCl, 5 mM $MgCl_2$, 4 mM Tris-HCl, 0.6 mM EDTA, 0.6 mM DTT. The products of the reaction were resolved by electrophoresis through a 0.75 mm thick, 5% polyacrylamide gel in TBE buffer (89 mM tris-HCl, pH 8, 89 mM borate, 2 mM EDTA) at 150 Volts. The gels were dried onto DE81 filter paper and autoradiographed. As a positive control for XPE-BF, a nuclear preparation from the human HeLa cell line was also assayed.

Binding of XPE-BF from the HeLa nuclear extract to damaged DNA is shown as a band of retarded mobility. Binding activity from the K-1735 TK melanoma clones electrophoresed with a similar mobility to that of the HeLa Cells. The binding activity was demonstrated to be specific for damaged DNA. Therefore, the binding activity in the K-1735 TK clones appeared to be the murine homolog of XPE-BF. The amount of murine XPE-BF in the control 2-4 cells was greater than that of the NM23-1 expressing 4-6 cells. From another transfection experiment, the amount of XPE-BF in the control A2 clone was greater than that of the NM23-1 expressing A3 clone. Thus, increased expression of NM23 in transfected TK murine melanoma cells was associated with decreased nuclear XPE binding factor levels.

EXAMPLE 2
Effect of NM23 expression on murine melanoma sensitivity to the chemotherapeutic drug cisplatin.

Figure 2:
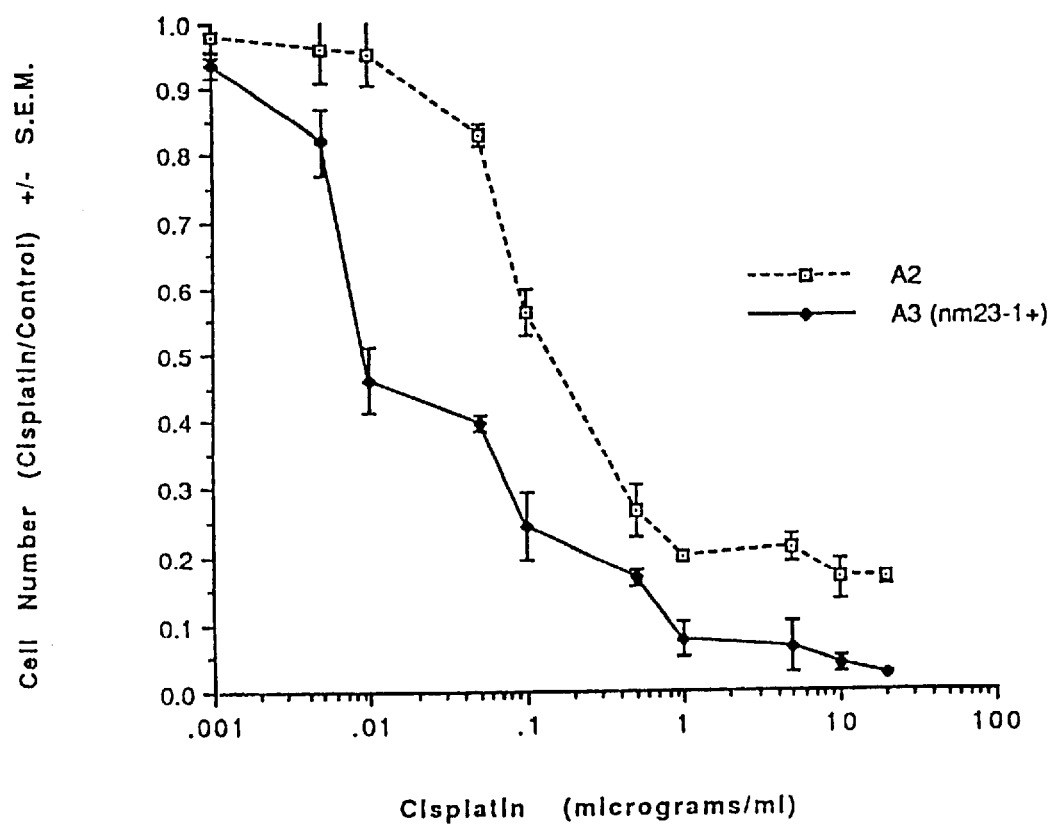
FIG. 2 shows cisplatin sensitivity of the murine K1735 TK control A2 and NM23 expressing A3 cell clones in vitro.

FIG. 1 demonstrates the sensitivity of the NM23-1 expressing 4-6 and control 2-4 K-1735 TK melanoma clones to cisplatin in vitro. FIG. 2 demonstrates the sensitivity of the NM23-1 expressing A3 and contro A2 K-1735 TK melanoma clones to cisplatin in vitro. In these experiments $8 \times 10^4$ viable tumor cells from each line were plated in TC24 tissue culture dishes in 0.9 ml of complete medium (Dulbecco's MEM containing antibiotics, glutamine, 10% fetal calf serum) and incubated at 37° C. for several hours to permit cell attachment to the tissue culture dishes. Cisplatin, obtained from the National Institutes of Health Pharmacy, was diluted in water as per the manufacturer's specifications. Aliquots were stored at −70° C. in a light-protected container, and thawed one time for usage. Potency was stable for approximately one month of storage and decreased afterwards. Cisplatin, at doses ranging from 20 µml to 1 µml final concentration, was added to the cultures. Control cultures did not receive cisplatin. The cultures were incubated for two days. Cell number and viability were determined by removing the culture medium, trypsinization of the cells, and counting viable cells/ml in trypan blue using a hemocytometer. Duplicate or triplicate cultures were counted at each cisplatin concentration, depending on the experiment. The number of viable cells at each dose of cisplatin was divided by the number of viable control cells. K-1735 TK clones were also incubated for up to five days of culture in cisplatin, and similar inhibition data were observed.

As shown on FIG. 1, control 2-4 cells exhibited a dose-dependent inhibition of growth in cisplatin, with an $ID_{50}$ (dose of cisplatin that inhibits 50% of cell growth) of approximately 400 ng/ml. Cells of the 4-6 clone, which differ from 2-4 by their increased expression of NM23, exhibited an $ID_{50}$ of approximately 110 ng/ml, and were therefore much more sensitive to the inhibitory effects of this drug.

The control 2-4 clone exhibited complete resistance to cisplatin in this assay at approximately 70 µg/ml. In contrast, complete resistance to cisplatin was observed at approximately 1 ng/ml by the NM23 expressing 4-6 cell clone. The development of drug resistant cells is considered to be one of the major reasons for cancer treatment failure, and the level of complete resistance is relevant to clinical usefulness. However, by both measurements, NM23 expression increased the melanoma cells' sensitivity to cisplatin.

The graph of FIG. 2 illustrating the K-1735 TK melanoma control A2 clone and NM23-1 expressing A3 clone sensitivity to cisplatin confirm these data. The control A2 clone exhibited an $ID_{50}$ at approximately 180 ng/ml cisplatin, while the corresponding NM23 expressing A3 clone exhibited an $ID_{50}$ of approximately 11 ng/ml. The control A2 clone exhibited a broad shoulder of near complete resistance to cisplatin, extending from 10 ng/ml. Near-complete resistance of the NM23 expressing A3 clone was observed at 1 ng/ml cisplatin.

EXAMPLE 3
Effect of NM23 expression on the sensitivity of human breast carcinoma sensitivity to the chemotherapeutic drug cisplatin.

The publicly available MDA-MB-435 cell line was derived from a pleural effusion of human breast carcinoma, and exhibits both tumorigenic and metastatic behavior upon injection into the mammary fat pad of nude mice. To test the effect of NM23 expression on cisplatin sensitivity, the MDA-435 cell line was transfected with one of two constructs: (a) a pCMVneo Bam construct that contained a CMV promoter (the pCMVneo Bam construct was previously published (Baker et al., Science 249:912–915 (1990)), but without an adjoining gene to be expressed; (b) the same pCMVneo Bam vector, into which the human nm23-H1 cDNA (Rosengerdet et al., Nature 342:177–180 (1989)) was cloned next to the CMV promoter by blunt end ligation into the Bam HI site. Ligated plasmid was transformed into bacteria, and minipreps tested by restriction endonuclease digestion and agarose gel electrophoresis. All constructs contained a neomycin resistance marker gene. MDA-435 cells were transfected with either vector using the standard calcium phosphate method. Neomycin resistant, nm23-H1 transfected clones were examined for the presence of an exogenous (higher molecular weight) nm23 transcript observable on Northern blots. Two control transfected clones, C-100 and C-103, were randomly selected from neomycin resistant, control transfected colonies. Two nm23-H1 transfected clones, H1-177 and H1-170, expressed high levels of NM23-H1 protein as compared to the control clones, determined by immunoprecipitation of pulse labelled NM23 protein and Western blot analyses.

Figure 3:
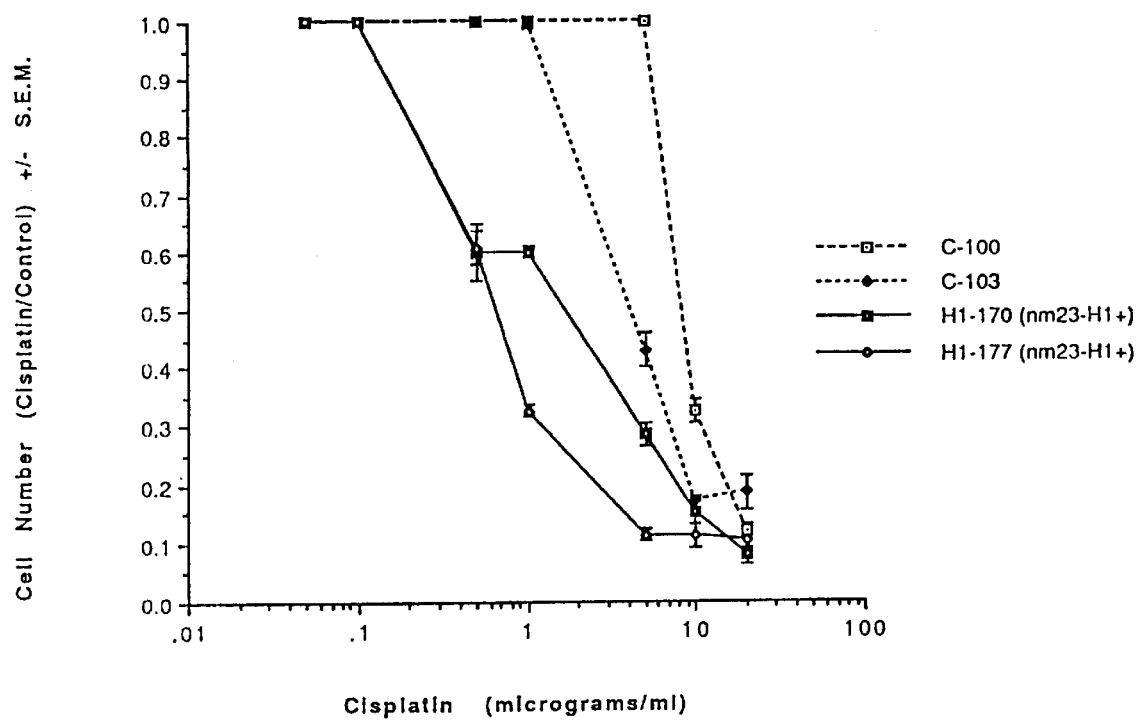
FIG. 3 shows cisplatin sensitivity of the control C-100 and C-103 clones, and the NM23-H1 expressing H1-170 and H1-177 clones of the human MDA-MB-435 breast carcinoma cell line in vitro.

FIG. 3 demonstrates the cisplatin sensitivity of the control C-100 and C-103 and NM23-H1 expressing H1-170 and H1-177 clones in vitro. The control clones exhibited $ID_{50}$ of 5–10 g/ml of cisplatin, while H1-170 and H1-177 exhibited $ID_{50}$ of 0.75–2.0 g/ml cisplatin, respectively. Expression of the human NM23-H1 protein therefore increased cisplatin sensitivity in a human breast carcinoma cell line. Like the murine melanoma cell lines, the data are more striking when cisplatin resistance is considered. The control clones developed complete resistance to cisplatin at approximately 1.5–7

µg/ml cisplatin, while the NM23-H1 expressing clones exhibited resistance at approximately 140 ng/ml cisplatin.

Although the invention has been described with reference to the presently-preferred embodiment, it should be understood that various modifications can be made without departing from the spirit of the invention. Accordingly, the invention is limited only by the following claims.

What is claimed is:

1. A method of increasing the sensitivity of a cell to a DNA damaging agent made more effective by an increased amount of NM23 in the cell, comprising increasing the amount of NM23 in the cell.

2. The method of claim 1, wherein the amount of NM23 is increased by a transcription enhancing vector.

3. The method of claim 1, wherein the damaging agent is a chemotherapeutic.

4. The method of claim 3, wherein the chemotherapeutic is cisplatin.

5. The method of claim 1, wherein the damaging agent is radiation.

6. The method of claim 1, wherein the NM23 is NM23-H1.

7. The method of claim 1, wherein the NM23 is NM23-H2.

8. The method of claim 1, wherein the cell is a tumor cell.

9. The method of claim 8, wherein the tumor cell is a melanoma cell.

10. The method of claim 8, wherein the tumor cell is a carcinoma cell or sarcoma cell.

11. A method of screening drugs for chemotherapeutic DNA damaging activity comprising determining the amount of NM23 produced by a cell selecting a cell having low NM23, contacting the drug with the cell and determining the effect on the cell.

12. A method of predicting resistance in a cell to a DNA damaging agent made more effective by an increased amount of NM23 in the cell comprising detecting the amount of NM23 expression in a cell, correlating the amount to an amount for a resistant cell, the presence of NM23 in an amount about equal to or less than the resistant cell indicating resistance.

13. A method of predicting a patient's response to a DNA damaging therapy made more effective by an increased amount of NM23 in a cell, to a tumor cell from the patient, comprising obtaining a tumor cell from the patient, determining the amount of NM23 in the cell, correlating the amount of NM23 in the cell to an amount in cells susceptible to the therapy, the presence of NM23 in an amount about equal to or greater than a susceptible cell indicating responsiveness to the therapy.

14. A kit for modulating the sensitivity of a cell to a DNA damaging agent made more effective by an increased amount of NM23 in the cell, comprising a means to enhance transcription of NM23 in an amount to increase the sensitivity of the cell to the agent, a DNA damaging agent, and a pharmaceutically acceptable carrier.

15. A kit for detecting the susceptibility of a cell to a DNA damaging therapy made more effective by an increased amount of NM23 in the cell, comprising a means to detect the amount of NM23 in the cell and a DNA damaging agent made more effective by an increased amount of NM23 in the cell correlate the amount of NM23 to an amount known to be susceptible to DNA damaging.

16. The kit of claim 15, wherein the means to detect the amount of NM23 includes an antibody specifically reactive with NM23.

17. A method of increasing the sensitivity of a cell ex vivo to a DNA damaging agent comprising increasing the amount of NM23 in the cell.

* * * * *